United States Patent [19]

Katsuyama et al.

[11] Patent Number: 4,478,942
[45] Date of Patent: Oct. 23, 1984

[54] QUANTITATIVE ANALYSIS FILM AND A METHOD FOR COLORIMETRIC ANALYSIS USING THE SAME

[75] Inventors: Harumi Katsuyama; Yoshikazu Amano; Asaji Kondo, all of Saitama, Japan

[73] Assignee: Fuji Photo Film Co., Ltd., Saitama, Japan

[21] Appl. No.: 352,969

[22] Filed: Feb. 26, 1982

[30] Foreign Application Priority Data

Feb. 27, 1981 [JP] Japan .................. 56-028158

[51] Int. Cl.³ .................. G01N 33/52; C12Q 1/28
[52] U.S. Cl. .................. 436/66; 422/56; 435/28; 435/805; 436/135; 436/170; 436/904
[58] Field of Search .................. 435/16, 25, 28, 805; 422/56, 57, 58; 436/66, 95, 170, 135, 904

[56] References Cited

U.S. PATENT DOCUMENTS

| | | | |
|---|---|---|---|
| 3,867,258 | 2/1975 | Forgione | 435/805 X |
| 4,029,598 | 6/1977 | Neisius et al. | 422/56 X |
| 4,042,335 | 8/1977 | Clement | 422/56 |
| 4,066,403 | 1/1978 | Bruschi | 422/57 X |
| 4,153,668 | 5/1979 | Mill et al. | 422/56 |
| 4,166,093 | 8/1979 | Smith-Lewis et al. | 422/56 |
| 4,260,679 | 4/1981 | Tsuda et al. | 436/95 X |
| 4,283,491 | 8/1981 | Dappen | 422/56 X |

Primary Examiner—Arnold Turk
Attorney, Agent, or Firm—Sughrue, Mion, Zinn, Macpeak & Seas

[57] ABSTRACT

A quantitative analysis film comprising a reagent layer comprising a cationic dye-forming color indicator for detecting hydrogen peroxide and an anionic polymer. By the use of such a color indicator and an anionic polymer in combination, a cationic dye is formed; the formed cationic dye is then bound and fixed to the anionic polymer to provide an intensified color. A method for the colorimetric assay of hydrogen peroxide or a precursor thereof with high sensitivity and high efficiency is also disclosed.

18 Claims, 8 Drawing Figures

QUANTITATIVE ANALYSIS FILM AND A METHOD FOR COLORIMETRIC ANALYSIS USING THE SAME

BACKGROUND OF THE INVENTION

Field of the Invention

The present invention relates to a dry type quantitative analysis film comprising a color indicator composition for detecting hydrogen peroxide, more particularly, to a dry type quantitative analysis film comprising a cationic dye forming color indicator composition for detecting hydrogen peroxide and an anionic polymer. The present invention further relates to a colorimetric quantitative analysis method using a color indicator composition for detecting hydrogen peroxide and an anionic polymer in combination.

Development of the Invention

Various quantitative analysis films, particularly multi-layered analysis films which permit colorimetric analysis of hydrogen peroxide by dry procedures, have been proposed and some of them have been put in practical use. Among them, there are quantitative analysis films for analysis of glucose, uric acid, cholesterol, choline esterase, creatine, etc., in the living body by dry procedure which comprises, in sequence, reacting the same with the appropriate oxidizing enzyme or reacting the reaction product formed during an enzyme reaction with the appropriate oxidizing enzyme, reacting the thus released hydrogen peroxide with a color indicator to form color, and then measuring the formed color. In order to enhance the speed of examination, avoid complicated operation and reduce cost, demands for dry type quantitative analysis films have increased, particularly in the field of clinical examination. Thus, quantitative analysis films of the test paper sheet type of the single, or layers or multi-layered quantitative analysis type of high accuracy in analysis have been developed.

In particular, multi-layer composite type quantitative analysis films are disclosed in Japanese Patent Application (OPI) (the term "OPI" as used herein refers to a "published unexamined Japanese patent application) No. 53888/74 (corresponding to U.S. Pat. No. 3,992,158) have markedly improved accuracy in analysis as compared to conventional quantitative analysis films of the test paper sheet type having a single or dual layers. For purposes of further improving accuracy in analysis and in accordance with the analyte to be assayed, hydrogen peroxide indicators having high detection sensitivity have also been provided in such multi-layer composite type quantitative analysis forms; examples of indicators for detecting hydrogen peroxide and layer structures for such multi-layer analysis films are disclosed in Japanese Patent Application (OPI) Nos. 40191/76 (corresponding to U.S. Pat. No. 4,042,335) 131089/78, 29700/79 (corresponding to U.S. Pat. No. 4,166,093), 124499/80, etc.

Indicators for detecting hydrogen peroxide used for these quantitative analysis films by a dry procedure are based on those for detecting hydrogen peroxide employed in conventional quantitative analysis by a dry procedure and the principles are the same.

Particularly, in the field of clinical examination, a variety of components in the living body are converted into common intermediates through chemical reactions having high specificity, generally utilizing an enzyme reaction having particularly high specificity, to thereby effect quantitative determination. As such a common intermediate, hydrogen peroxide has been utilized in many measurement methods. Further, many colorimetric methods which are inexpensive and promise high accuracy have been developed based on combinations of hydroperoxidase—where substrate is hydrogen peroxide—and related reagents.

Catalase or peroxidase (POD) is often used as hydroperoxidase and, in particular, many combinations with indicators for detecting hydrogen peroxide utilizing peroxidation of peroxidase are known. Indicators for detecting hydrogen peroxide are classified into two groups: (a) reducible chromogens and (b) combination of a hydrogen donor (developing agent) and a coupler. The former was proposed by Keston, A. S., et al. (Keston, A. S., *Specific Colorimetric Enzymatics Analytical Reagents for Glucose*, Abstracts of Papers, 129th Meeting Am. Chem. Soc. page 31C, April (1956), and the latter by P. Trinder (*Ann. Cli. Biochem.*, 6, 24 (1969) and *J. Clin. Pathol.*, 22, 246 (1969)). Improvement on such reducible chromogens, hydrogen donors or couplers are disclosed in Japanese Patent Publications Nos. 33798/72, 16235/79, 37555/76, 44834/78, 12360/79, 24879/80 and 3394/79, Japanese Patent Applications (OPI) Nos. 86392/77, 26188/78, 50991/74, 11892/75, 40585/78, 110897/80, 25892/79, 20471/80 and 101861/80, Japanese Patent Publication No. 2960/80, etc.

In conventional multi-layer analysis films, methods for fixing the dye formed, based on mordanting an acidic dye using a high molecular weight quaternary ammonium salt have been based on the art of instant color photography per se or by appropriately modifying the same, and such have been used for forming a dye from an indicator for detecting hydrogen peroxide and fixing the resulting dye. In Japanese Patent Application (OPI) No. 40191/76 (corresponding to U.S. Pat. No. 4,042,335), 1-naphthol-2-sulfonic acid is used as a coupler and a quaternary ammonium salt (e.g., polyvinylpyridine, a quaternary ammonium salt of a polymer) as a mordanting agent in a detection layer; in Japanese Patent Application (OPI) No. 29700/79 (corresponding to U.S. Pat. No. 4,166,093), using a similar mordanting agent in a migration-prevention layer present between a reagent layer and a radiation blocking porous layer is disclosed; in Japanese Patent Application (OPI) No. 131089/78, using a similar mordanting agent in a layer receiving a diffusible and detectable material by allowing a non-diffusible substance comprising a detectable material previously formed to diffuse by the action of an analyte is disclosed.

However, mordanting agents for acidic dyes such as polyvinylpyridine or high molecular weight substances containing quaternary ammonium salts involve two serious disadvantages.

A first disadvantage is, as is described in Japanese Patent Application (OPI) No. 29700/79 (corresponding to U.S. Pat. No. 4,166,093), that the presence of a mordanting polymer in a reagent layer results in a marked decrease in detection sensitivity, i.e., basic cationic compounds have a marked inhibition against enzymes.

A second disadvantage is based on the fact that a position where a mordanting effect is exhibited is the binding site of a sulfonic acid group, a carboxylic acid group, a phenolic hydroxy group or a salt thereof, which is bound to the dye formed, and thus the corresponding dye precursor is also bound and fixed to the mordanting polymer as in the formed dye and detection sensitivity is reduced. This is because these substituents are not directly correlated to the coupling reaction system involved in dye color formation i.e., as there is no chance for these substituents to be formed during the dye forming reaction, a substituent exhibiting a mordanting effect must necessarily be introduced in dye precursor. When a reactive dye precursor is fixed to a polymer, reaction rate and reactivity are markedly reduced due to the steric hindrance of the high molecular chain, and such is a well known effect ordinarily occurring in reactions involving high molecular weight substances; in quite a similar fashin, a reduction in detection sensitivity occurs.

SUMMARY OF THE INVENTION

An object of the present invention is to provide a multilayer analysis film in which mobility of dye formed is prevented in multilayer analysis elements for detecting hydrogen peroxide to thereby improve accuracy.

Another object of the present invention is to provide a reagent composition for an oxidative coupling reaction capable of forming a cationic dye having high absorbancy to enhance detection sensitivity.

A further object of the present invention is to provide a novel fixing agent comprising an anionic polymer.

A further object of the present invention is to provide a dye-fixing agent comprising an anionic polymer which does not substantially inhibit enzyme reaction.

A further object of the present invention is to provide a dye-fixing agent comprising an anionic polymer having specificity which does not react with any dye precursor contained in an indicator composition for detecting hydrogen peroxide but reacts only with a formed dye and possesses the capability of fixing the dye.

Another object of the present invention is to provide a colorimetric method for assaying hydrogen peroxide and its precursors with good efficiency and high sensitivity which comprises forming a cationic dye using of an indicator composition for detecting hydrogen peroxide capable of forming a cationic dye and an anionic polymer (in combination) and binding the resulting cationic dye to the anionic polymer to thereby fix the dye.

The present invention is directed to:

(1) A quantitative analysis film comprising a reagent layer containing a cationic dye-forming color indicator composition for detecting hydrogen peroxide containing a component capable of forming the cationic dye by chemical interaction in the presence of hydrogen peroxide, and an anionic polymer.

Main embodiments include:

(2) A quantitative analysis film as described in (1) wherein the reagent layer comprises a color forming reaction layer and a dye-fixing layer containing the anionic polymer;

(3) A quantitative analysis film as described in (1) wherein the reagent layer is a single layer;

(4) A quantitative analysis film as described in (1), (2) or (3) wherein the color indicator composition is a color indicator composition comprising, as main ingredients, a substance having peroxidase activity, a hydrogen donor and an N,N-disubstituted aniline;

(5) A quantitative analysis film as described in (1), (2), (3) or (4) wherein the anionic polymer is a polymer containing a carboxylate group, a sulfonate group or a phosphonate group;

(6) A quantitative analysis film for quantitative determination as described in (4) or (5) wherein the N,N-disubstituted aniline is a compound represented by formula (1):

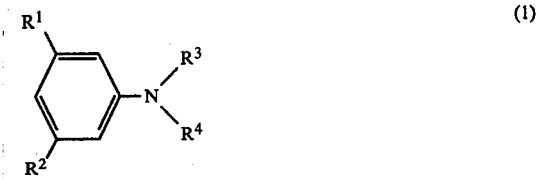

In formula (1), $R^1$ and $R^2$ each represents a hydrogen atom, an alkyl group or an alkoxy group and $R^1$ and $R^2$ may be the same or different from each other; $R^3$ and $R^4$ represent an alkyl group, an alkoxyalkyl group, a hydroxyalkyl group, an aminoalkyl group, a cyanoalkyl group, a halogenoalkyl group or an acylaminoalkyl group and $R^3$ and $R^4$ may be the same or different from each other.

(7) A quantitative analysis film as described in (4), (5) or (6) wherein the hydrogen donor is a compound selected from the group consisting of a compound represented by formula (2) below, a 4-substituted antipyrine, a 2-hydrazonobenzothiazoline and a p-halogenophenol.

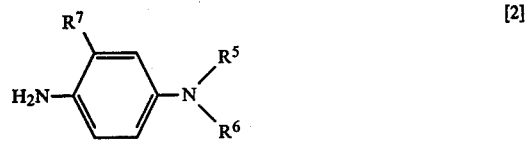

In formula (2), $R^5$ and $R^6$ represent an alkyl group, an alkoxyalkyl group, a hydroxyalkyl group, a cyanoalkyl group, a halogenoalkyl group or an acylaminoalkyl group and, $R^5$ and $R^6$ may be the same or different; $R^7$ represents a hydrogen atom, an alkyl group, an alkoxy group or a halogen atom.

(8) A quantitative analysis film as described in (4), (5) or (6) wherein the hydrogen donor is 4-aminoantipyrine.

(9) A quantitative analysis film as described in (1), (2), (3), (4), (5), (6) or (7) wherein the reagent layer is provided between a support and a porous layer and the porous layer is adhered to the reagent layer in fluid contact as a united or integral composite.

(10) A colorimetric method for quantitative analysis which comprises colorimetrically assaying hydrogen peroxide or a precursor capable of forming hydrogen peroxide contained in a testing sample, the method comprises the steps of bringing the testing sample into contact with a cationic dye-forming color indicator composition containing a component capable of forming a cationic dye by chemical interaction in the presence of hydrogen peroxide and binding the formed cationic dye to the anionic polymer.

Main embodiments thereof are:

(11) A colorimetric method for quantitative analysis as described in (10) wherein the anionic polymer is previously present with the color indicator composition for detecting hydrogen peroxide.

(12) A colorimetric method for quantitative analysis as described in (10) wherein the anionic polymer is brought into contact with and bound to the cationic dye after the cationic dye is formed.

BRIEF DESCRIPTION OF THE DRAWINGS

In FIGS. 1 to 8, the numerals have the following meaning:
- 10: support
- 20: reagent layer
- 21: dye-fixing layer
- 22: color-forming reaction layer
- 23: support impregnated with reagents
- 31: porous spreading layer
- 32: definite area-porous layer
- 40: light-reflecting layer

DESCRIPTION OF PREFERRED EMBODIMENTS

Figure 1:
FIGS. 1 through 8 represent cross-sectional views of embodiments of quantitative analysis film in accordance with the present invention.

In the specification, the term "reagent layer" is used to refer to a layer in which an analyte is converted into a chemically detectable species and which contributes to improvement in a detection efficiency of the chemically detectable species. The reagent layer contains a cationic dye-forming color indicator composition for detecting hydrogen peroxide and an anionic polymer.

The term "color-forming reaction layer" refers to a layer in which an analyte is converted into a chemically detectable species.

The term "dye-fixing layer" refers to a layer which contributes to improvement in a detection efficiency of the chemically detectable species.

The reagent layer can be a color-forming reaction and dye-fixing layer when the reagent layer is a single layer and, the reagent layer can also be divided into at least two layers, one of which is a color-forming reaction layer and another is a dye-fixing layer. In other words, a color-forming reaction layer and a dye-fixing layer can also be collectively referred to as a reagent layer.

The chemically detectable species is directly or indirectly indicative of the presence and/or concentration of a desired analyte, or a reaction or decomposition product of the analyte.

The term "substance having peroxidase activity" is used to mean a substance which catalyzes oxidation of a hydrogen donor with hydrogen peroxide (as a substrate) and well recognized in the art (I. Yamazaki et al., MOLECULAR & CELLULAR BIOCHEMISTRY, vol. 2(1), pp. 39–52 (1973)). The substance having peroxidase activity takes part in the oxidation of a hydrogen donor with hydrogen peroxide in accordance with the following reation scheme:

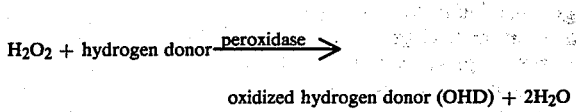

oxidized hydrogen donor (OHD) + 2H$_2$O

The term "hydrogen donor" refers to a compound which is an oxygen acceptor which, in its oxidized state, couples with the N,N-disubstituted anilines of formula (1).

The cationic dye-forming color indicator composition for detecting hydrogen peroxide containing a component capable of producing a cationic dye by chemical interaction in the presence of hydrogen peroxide (hereafter referred to as a "color indicator for detecting hydrogen peroxide") is an indicator composition comprising, as main ingredients, a substance having a peroxidase activity, a hydrogen donor and an N,N-disubstituted aniline.

Examples of substances having peroxidase activity include peroxidase extracted from various organisms, synthetic peroxidase and other chemical substances extracted from organisms which exhibit an activity similar to peroxidase, as disclosed in Japanese Patent Application (OPI) No. 137192/75. Of these, peroxidase is preferred.

As hydrogen donors which are contained in the color indicator, 4-substituted antipyrines (4-substituted-2,3-dimethyl-1-phenyl-3-pyrazolin-5-ones) as disclosed in Japanese Patent Application (OPI) No. 50991/74 (corresponding to U.S. Pat. No. 3,983,005) and other known 4-substituted antipyrines; N,N-disubstituted-o- or p-phenylenediamines as disclosed in Japanese Patent Application (OPI) No. 137192/75 (corresponding to U.S. Pat. No. 3,886,045) and other known N,N-disubstituted-o- or p-phenylenediamines; 2-hydrazonobenzothiazolines as disclosed in Japanese Patent Application (OPI) No. 20471/80 and other known 2-hydrazonobenzothiazolines; p-halogenophenols as disclosed in Japanese Patent Application (OPI) No. 148100/80 and other p-halogenophenols and N,N-disubstituted phenylenediamines as represented by formula (2) above can be employed.

Specific examples of useful 4-substituted antipyrines include 4-aminoantipyrine (CAS Registry Number (83-07-8); hereafter the same), 4-(dimethylamino)antipyrine (pyramidon (58-15-1)), 4-(ethylaminoantipyrine) (15166-10-6), 4-(methylamino)antipyrine (noramidopyrine, (519-98-2)), 4-(sodium sulfonatomethylamino)antipyrine (sulphamipyrine (129-89-5)), 4-((sodiumsulfonatomethyl) (isobutyl)aminoantipyrine (dibupyrone (1046-17-9)), 4-(sodium sulfonatomethyl) (methyl)amino antipyrine (methampyrone, (5907-38-0)) and 4-isopropylantipyrine (propiphenazone, (479-92-5)). As other compounds having a similar structure, there are 4-amino-2,3-dimethyl-1-p-tolyl-3-pyrazolin-5-one (56430-10-5) and 4-amino-1,3-diphenyl-2-methyl-3-pyrazolin-5-one (52744-73-7). Also, 2-(dimethylamino)-5-phenyl-2-oxazolin-4-one (tozalinone, (1046-17-9)) can be employed.

In the case where substituents R$^5$ and R$^6$ in N,N-disubstituted-p-phenylenediamines represented by formula (2) are an alkyl group, the alkyl group can be a straight or branched lower alkyl group having 1 to 5 carbon atoms; specific examples thereof include a methyl group, an ethyl group, a propyl group, a butyl group, a pentyl group, an isopropyl group, an isobutyl group, an isoamyl group, a t-butyl group and a neopentyl group. In the case of an alkoxyalkyl group, the alkoxyalkyl group comprises a lower alkyl group having 1 to 3 carbon atoms on which a lower alkoxy group having 1 to 3 carbon atoms in substituted; specific examples include a methoxymethyl group, a 2-methoxyethyl group, a 1-methoxyethyl group, a 3-methoxypropyl group, a 2-methoxypropyl group, an ethoxypropyl group and a 2-ethoxyethyl group. In the case of a hydroxyalkyl group, the hydroxyalkyl group comprises a straight or branched lower alkyl group having 1 to 5 carbon atoms on which a hydroxyl group is substituted; specific examples include a hydroxymethyl group, a 2-hydroxyethyl group, a 1-hydroxyethyl group, a 3-hydroxypropyl group, a 2-hydroxypropyl group, a 4-hydroxybutyl group and a 5-hydroxypropyl group. In the case of a cyanoalkyl group, the cyanoalkyl group comprises a straight or branched lower alkyl group having 1 to 5 carbon atoms on which a cyano group is substituted; specific examples thereof include a cyanomethyl group, a 2-cyanoethyl group, a 1-cyanoethyl group, a 3-cyanopropyl group, a 2-cyanopropyl group and a 5-cyanopentyl group. In the case of a halogenoalkyl group, the halogenoalkyl group comprises a straight or branched lower alkyl group having 1 to 5 carbon atoms on which a fluorine, chlorine, bromine or iodine atom is substituted as a halogen atom; specific examples thereof include a fluoromethyl group, a chloromethyl group, a bromomethyl group, a 2-fluoroethyl group, a 1-chloroethyl group, a 2-chloroethyl group, a 2-bromoethyl group and a 3-chloropropyl group. In the case of an acylaminoalkyl group, the acylaminoalkyl group comprises a straight or branched lower alkyl group having 1 to 5 carbon atoms on which an acetamido group, a propionamido group, a benzamido group, a toluamido group, a methanesulfonamido group, a benzenesulfonamido group or a toluenesulfonamido group is substituted as an acylamino group (1 to 10 carbon atoms); specific examples include an acetamidomethyl group, a propionamidomethyl group, a benzamidomethyl group, a p-toluamidomethyl group, a methanesulfonamidomethyl group, an ethanesulfonamidomethyl group, a benzenesulfonamidomethyl group, a p-toluenesulfonamidomethyl group, a 2-acetamidoethyl group, a 2-propionamidoethyl group, a 2-benzamidoethyl group, a 2-p-toluamidoethyl group, a 2-methanesulfonamidoethyl group, a 2-(ethanesulfonamido)ethyl group, a 2-(benzenesulfonamido)ethyl group, a 2-(p-toluenesulfonamido)ethyl group, a 3-acetamidopropyl group and a 3-benzamidopropyl group.

Specific examples of preferred $R^5$ and $R^6$ include a methyl group, an ethyl group; a methoxymethyl group, a 2-methoxyethyl group, an ethoxymethyl group, a 2-ethoxyethyl group; a hydroxymethyl group, a 2-hydroxyethyl group, a 1-hydroxyethyl group, a 2-hydroxypropyl group; an acetamidomethyl group, a 2-acetamidoethyl group, a methanesulfonamidomethyl group, a 2-methanesulfonamidoethyl group; a chloromethyl group, a 2-chloroethyl group; a cyanomethyl group and a 2-cyanoethyl group.

In the case substituent $R^7$ in N,N-disubstituted-p-phenylenediamines represented by formula (2) is an alkyl group, specific examples thereof are the same as the specific examples in the case where $R^5$ and $R^6$ are an alkyl group. In the case $R^7$ is an alkoxy group, the alkoxy group is an alkoxy group comprises a straight or branched lower alkyl group having 1 to 5 carbon atoms and specific examples include a methoxy group, an ethoxy group, a propoxy group, an isopropoxy group, a butoxy group, an isobutoxy group, a pentyloxy group and an isoamyloxy group. In the case $R^7$ is an halogen atom, specific examples include a fluorine atom, a chlorine atom, a bromine atom and an iodine atom.

Preferred substituents as $R^7$ are a hydrogen atom, an alkyl group (1 to 5 carbon atoms) and halogen atom; the alkyl group is specifically a methyl group, an ethyl group or a propyl group and the halogen atom is specifically a fluorine atom or a chlorine atom.

Specific examples of N,N-disubstituted-p-phenylenediamines represented by formula (2) include the following compounds:
N,N-Dimethyl-p-phenylenediamine
N,N-Diethyl-p-phenylenediamine
N-Ethyl-N-(β-hydroxyethyl)-p-phenylenediamine
N-Ethyl-N-(β-ethoxyethyl)-p-phenylenediamine
N-Ethyl-N-(β-methanesulfonylaminoethyl)-3-methyl-4-aminoanidine
N-ethyl-N-(β-hydroxyethyl)-3-methyl-4-aminoaniline
N-ethyl-N-(β-cyanoethyl)-p-phenylenediamine
N-Ethyl-N-(β-chloroethyl)-p-phenylenediamine
N-Ethyl-N-(β-ethoxyethyl)-p-phenylenediamine
N,N-Diethyl-3-chloro-4-aminoaniline
N,N-Bis(β-cyanoethyl)-p-phenylenediamine As hydrogen donors, 4-substituted antipyrines and N,N-disubstituted-p-phenylenediamines represented by formula (2) are preferred. Of these, 4-aminoantipyrine, N,N-dimethyl-p-phenylenediamine and N,N-diethyl-p-phenylenediamine are particularly preferred.

In the case substituents $R^1$ and $R^2$ in the N,N-disubstituted aniline represented by formula (1) represent an alkyl group or an alkoxy group, specific examples thereof are the same as the specific examples in the case that substituent $R^5$ or $R^6$ in the N,N-disubstituted-p-phenylenediamine represented by formula (2) described above represent an alkyl group or an alkoxy group.

In the case $R^3$ and $R^4$ represent an alkyl group, an alkoxyalkyl, a hydroxyalkyl group, a cyanoalkyl group, a halogenoalkyl group or an acyalminoalkyl group, specific examples thereof are the same as the specific examples in the case where $R^5$ or $R^6$ represent an alkyl group, an alkoxyalkyl group, a hydroxyalkyl group, a cyanoalkyl group, a halogenoalkyl group or an acylaminoalkyl group. In the case $R^3$ and $R^4$ represent an aminoalkyl group, the aminoalkyl group comprises a straight or branched lower alkyl group having 1 to 5 carbon atoms on which an amino group is substituted; specific examples include an aminomethyl group, a 2-aminoethyl group, a 1-aminoethyl group, a 3-aminopropyl group and a 2-aminopropyl group.

Preferred substituents as $R^1$ and $R^2$ are a hydrogen atom, an alkyl group (1 to 5 carbon atoms) and an alkoxy group (1 to 3 carbon atoms); specific examples of the alkyl group are a methyl group, an ethyl group, a propyl group and, as the alkoxy group, there are a methoxy group and an ethoxy group.

Preferred substituents as $R^3$ or $R^4$ are an alkyl group, an alkoxyalkyl group, a hydroxyalkyl group, a cyanoalkyl group and a halogenoalkyl group; specific examples include a methyl group, an ethyl group, a propyl group; a methoxymethyl group, a 2-methoxyethyl group, a 3-methoxypropyl group, an ethoxymethyl group, a 2-ethoxyethyl group; a hydroxymethyl group, a 1-hydroxyethyl group, a 2-hydroxyethyl group, a 2-hydroxypropyl group, a 3-hydroxypropyl group; a cyanomethyl group, a 2-cyanoethyl group; a chloromethyl group, a 1-chloroethyl group, a 2-chloroethyl group, a 2-chloropropyl group, a 3-chloropropyl group, a bromomethyl group, a 2-bromomethyl group, a fluoromethyl group and a 2-fluoroethyl group.

Specific examples of N,N-disubstituted anilines represented by formula (1) include the following compounds:
N,N-Dimethylaniline
N,N-Diethylaniline
N-Methyl-N-hydroxymethylaniline
N-Methyl-N-(2-hydroxyethyl)aniline
N-Ethyl-N-(2-hydroxyethyl)aniline
N-Methyl-N-(2-methoxyethyl)aniline
N-Ethyl-N-(2-methoxyethyl)aniline
N-Ethyl-N-(2-ethoxyethyl)aniline
N,N-Dimethyl-m-toluidine
N,N-Diethyl-m-toluidine
N,N-Bis(hydroxymethyl)-m-toluidine N,N-Bis(2-hydroxyethyl)-m-toluidine
N,N-Bis(2-hydroxypropyl)-m-toluidine
N,N-Bis(3-hydroxypropyl)-m-toluidine
N-Methyl-N-hydroxymethyl-m-toluidine
N-Ethyl-N-2-hydroxyethyl-m-toluidine
N-Ethyl-N-hydroxymethyl-m-toluidine
N-Methyl-N-methoxymethyl-m-toluidine
N-Ethyl-N-methoxymethyl-m-toluidine
N-Ethyl-N-2-methoxyethyl-m-toluidine
N-Cyanomethyl-N-hydroxymethyl-m-toluidine
N-Methyl-N-2-chloroethyl-m-toluidine
N-Ethyl-N-2-chloroethyl-m-toluidine
N-2-Cyanoethyl-N-2-hydroxyethyl-m-toluidine
N,N-Dimethyl-m-anisidine Of these compounds, preferred N,N-disubstituted anilines are the following:
N,N-Bis(2-hydroxyethyl)-m-toluidine
N-Ethyl-N-2-hydroxyethyl-m-toluidine
N-2-Cyanoethyl-N-2-hydroxyethyl-m-toluidine
N,N-Dimethyl-m-anisidine
N,N-Diethyl-m-anisidine It is preferred that the color indicator for detecting hydrogen peroxide employed in the present invention not contain any cationic component compound which absorbs light (near ultraviolet rays, visible light or near infrared rays) having a wavelength region which the cationic dye formed by the chemical interaction in the presence of hydrogen peroxide absorbs, which would interfere with colorimetric analysis.

The anionic polymer employed in the present invention is a polymer containing the anionic group defined above in the polymer backbone itself or in the organic group (Org in formula (AP) below) bound to the polymer backbone. In addition to conventional anionic polymers, acid type cation ion exchange resins can also be employed as the anionic polymer; preferably the conventional anionic polymers or cation ion exchange resin are water-soluble polymers or polymers which are capable of being swollen by water (water-swellable). The anionic polymers can be employed singly or as a combination of two or more. Anionic polymers with and without film forming capability can both be employed but it is preferred that anionic polymers having no film-forming capability be employed in combination with binder polymers having film forming capability.

Specific examples of anionic polymers include polymers or copolymers having a structure where a carboxylate group (—COO$^\ominus$), a sulfonate group (—SO$_3^\ominus$) or a phosphonate group (—PO$_3^{2\ominus}$) is bound as an anionic atomic group, or the aforesaid anionic atomic group containing a counter cation is bound, to all of the constitutional repeating units (hereafter referred to as "CRU") of the high molecular chain thereof or to a part of the CRU (the arrangement may be either orderly or at random). As counter cations, there are alkali metal ions (e.g., Li$^\oplus$, Na$^\oplus$, K$^\oplus$, Cs$^\oplus$), alkaline earth metal ions (e.g., Mg$^{2\oplus}$, Ca$^{2\oplus}$, Sr$^{2\oplus}$, Ba$^{2\oplus}$) and ammonium ions (NH$_4^\oplus$).

These anionic polymers are shown by formula (AP):

Org—Q—Z$^\ominus$A$^\oplus$     (AP)

wherein Org represents an organic group and constitutes a portion of a polymer backbone, Q represents a chemical bond(s) or a chemical group linking Z$^\ominus$ to Org, Z$^\ominus$ represents a carboxylate group; (—COO$^\ominus$), a sulfonate group (—SO$_3^\ominus$) or a phosphonate group (—PO$_3^{2\ominus}$) and A$^\oplus$ is a counter cation as mentioned above.

Specific examples of anionic polymers containing the aforesaid CRU include the following:

Alkali hydrolysates of a methyl vinyl ether-maleic anhydride copolymer (copolymer containing dilithium, disodium or dipotassium 1,2-dicarboxylate ethylene as the CRU);

Alkali metal salt or alkaline earth metal salt of a polyacrylic acid;

Alkali metal salt or alkaline earth metal salt of a poly-N-($\beta$-sulfo-$\alpha,\alpha$-dimethylethyl)acrylamide;

Alkali metal salt or alkaline earth metal salt of a polystyrene-p-sulfonic acid;

Alkali metal salt or alkaline earth metal salt of a copolymer of styrene-p-sulfonic acid and a hydrophilic vinyl monomer (examples of hydrophilic vinyl monomers: acrylic acid, acrylic acid alkyl esters (e.g., methyl acrylate), acrylic acid hydroxyalkyl esters (e.g., $\beta$-hydroxyethyl acrylate), acrylamides (e.g., acrylamide, N-methylacrylamide, N-isopropylacrylamide, N-($\beta$-sulfonato-$\alpha,\alpha$-dimethylethyl)acrylamide, N-ethyl-N-isopropylacrylamide, acrylmorpholide

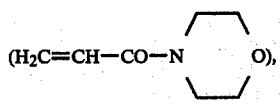

N-acryloylpiperidine, N-acryl oylpiperidine, N-acryloylpiperazine), methacrylic acid hydroxyalkyl esters (e.g., $\beta$-hydroxyethyl methacrylate), methacrylamides (e.g., methacrylamide, methacryl morpholide));

Alkali metal salts of a polyvinylphosphonic acid:

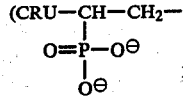

where M is lithium, sodium or potassium);
Carboxymethyl cellulose;
Carboxyethyl cellulose;
Alginic acid and alkali metal salts thereof;
Typical examples of preferred anionic polymers include the following:
Polystyrene-p-potassium sulfonate
Styrene-p-potassium sulfonate-acrylmorpholide copolymer
Styrene-p-potassium sulfonate-acrylamide copolymer
Styrene-p-potassium sulfonate-N-isopropylacrylamide copolymer
Styrene-p-sodium sulfonate-N-ethyl-N-isopropylacrylamide copolymer
Poly-N-($\beta$-potassium sulfonato-$\alpha,\alpha$-dimethyl)acrylamide
N-($\beta$-potassium sulfonato-$\alpha,\alpha$-dimethylethyl)acrylamide-$\beta$-hydroxyethyl acrylate copolymer
N-($\beta$-potassium sulfonato-$\alpha,\alpha$-dimethylethyl)acrylamide-N-ethylacrylamide copolymer Of these anionic polymers, polystyrene type anionic polymers (in formula (AP), Q is a phenylene group) are most preferred.

The anionic polymer can be incorporated into a layer containing the color indicator for detecting hydrogen peroxide or a dye-fixing layer containing the anionic polymer—but containing no other reagent component—can also be provided as a layer separately from a layer containing the color indicator for detecting hydrogen peroxide. Further, the anionic polymer can also be incorporated both into a layer containing the color indicator for detecting hydrogen peroxide and into the dye-fixing layer. The anionic polymer can also be employed as a combination of two or more thereof if desired or necessary, although only one is generally sufficient.

In the case that the anionic polymer is incorporated both into a layer containing the color indicator for detecting hydrogen peroxide and into the dye-fixing layer, both anionic polymers can be the same or they can differ. Further, if desired or necessary, the anionic polymer can also be incorporated into a layer other than a layer containing the color indicator for detecting hydrogen peroxide or a dye-fixing layer.

Any or all of the reagent layer containing the color indicator for detecting hydrogen peroxide and the anionic polymer, a color reaction layer containing the color indicator for detecting hydrogen peroxide and the dye-fixing layer containing the anionic polymer of the quantitative analysis film in accordance with the present invention can contain a binder polymer. As binder polymers, known hydrophilic polymers such as gelatin, casein, agarose, starch, polyvinyl alcohol, polyvinyl pyrrolidone, polyacrylamide, polyethylene glycol, etc., can be employed and, in combination with these hydrophilic polymers, known hardeners (hardening agents or cross linking agents) can also be employed.

The reagent layer, the color-forming reaction layer or the dye-fixing layer is formed either by dispersing or dissolving a mixture of the color indicator for detecting hydrogen peroxide and the anionic polymer or the color indicator for detecting hydrogen peroxide and the anionic polymer, respectively, in a binder polymer and then coating the dispersion or solution onto a support by a conventional coating technique followed by drying or by impregnating the surface of or the interior of a porous support with the dispersion or solution. In the case where the reagent layer, the color reaction layer or the dye-fixing layer is provided on a support by coating, the layer thickness of each is in a range of from 1 $\mu$m to 100 $\mu$m, preferably 2 $\mu$m to 50 $\mu$m. In the case that the dye-fixing layer is composed only of the anionic polymer free of any binder polymer, the layer thickness is in the range of from 1 $\mu$m to 50 $\mu$m, preferably 3 $\mu$m to 30 $\mu$m.

In the dye fixing method used in the quantitative analysis film of the present invention, a reactive group for fixation results for the first time upon the formation of a colored dye and, therefore, disadvantage encountered with conventional mordanting methods are eliminated. Further, surprisingly the fixing agent of the present invention does not substantially inhibit enzyme reactions so that it is possible to incorporate the same into a layer containing the color indicator for detecting hydrogen peroxide in which an enzyme reaction is performed.

In the present invention, a color-forming reaction caused in a layer containing the color indicator for detecting hydrogen peroxide in the presence of hydrogen peroxide is based upon the conventional reaction in which a cationic dye is produced by the oxidative coupling of a hydrogen donor (a typical example is a p-phenylenediamine derivative or 4-aminoantipyrine) and an aromatic amine. This method is described in the aforesaid James' publication and J. Kosar, *Light Sensitive Systems* (John Wiley & Sons., New York, 1965), pp. 215 to 259, etc.

In this reaction system, the coupler—which is a dye precursor—and the hydrogen donor are non-ionic compounds and do not participate in the fixing reaction onto the anionic polymer which is based on an ionic reaction. However, the cationic dye formed is strongly "dyed" or fixed onto the anionic polymer i.e., fixing capability is imparted to the dye only after the dye is formed.

Based on this principle, the fixing agent does not cause reaction before the dye is produced and a dye precursor can freely complete a dye-forming reaction in a layer containing the color indicator for detecting hydrogen peroxide without being fixed onto the polymer molecule.

It is disclosed in Japanese Patent Publication No. 5797/62 that the use of sodium alginate contributes to stabilize a binder composition for a test paper for detecting hydrogen peroxide which contains peroxidase and a chromogen and it is further disclosed in Japanese Patent Publication No. 1878/70 that color formed after oxidation is intensified in the presence of a binding agent consisting of an acid type and a partial ester type hydrolysate, of a methyl vinyl ether-maleic anhydride copolymer, polyvinyl pyrrolidone and 3,6-anhydro-D-galactose. It is also disclosed in Japanese Patent Publication No. 39558/75 and Japanese Patent Application (OPI) No. 120798/80 that a similar effect is achieved when a water/alcohol-treated methyl vinyl ether-maleic anhydride copolymer and polyvinyl pyrrolidone co-exist.

However, it has been found that increased intensity of color formation is not observed, rather diffusibility is merely minimized, in the reagent layer of the quantitative analysis film of the present invention. This difference is believed to be based on whether the formed dye is a basic nonionic dye (material disclosed in the patents described above) or a cationic dye (present invention). That is, color intensity has been increased due to cationization through protonation onto the nonionic dye. The color forming reagent layer of the test paper for quantitative analysis as described in the aforesaid patents is prepared by dipping a fibrous filter paper, etc., into reagents so that mobilization in the layer is substantially withdrawn from consideration. Thus, a system using such conventional test papers in which the density of the dye produced on a carrier such as filter paper, etc.—which is optically opaque—suffers a serious loss of accuracy based on the phenomenon described above; however, it is sufficient for quantitative analysis test paper to achieve such accuracy in measurement that is ignorable and for this reason, such a disadvantage has not been taken into account in the prior art.

In the preferred embodiment of the quantitative analysis film of the present invention, the reagent layer, the color-forming reaction layer or dye-fixing layer are coated layers which are optically transparent and have a constant thickness, and its function is equivalent to a microcuvette. The quantitative analysis film of the present invention aims at improving the aforesaid disadvantage encountered with conventional dry type analysis sheets and at providing an analysis method of higher accuracy. With such a quantitative analysis film, mobility of dye formed is eliminated since seriously harms accuracy. From such a viewpoint, a wide variety of polymers have been investigated and from these polymers, the anionic polymers of formula (AP) have been chosen and the present invention has been attained as such a result.

In the analysis film of the present invention, a cationic dye represented by formula (CD):

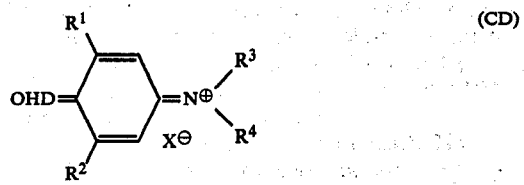

(CD)

wherein $R^1$ through $R^4$ represent the same meanings as in formula (1), $X^\ominus$ represents an anion and OHD represents the oxidized hydrogen donor moiety, is formed when a liquid sample is dropped onto the analysis film, and the cationic dye is then fixed by an anionic polymer contained in the analysis film.

Schemes of reactions which occur in the reagent layer of the quantitative analysis film of the present invention are expressed by formulae based on various embodiments of the present invention as follows:

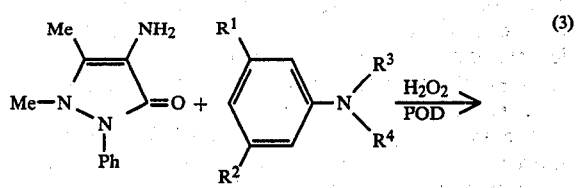

(3)

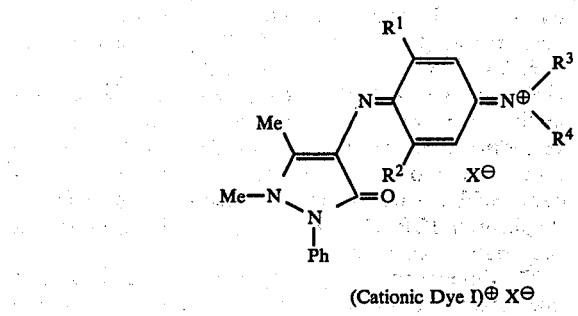

(Cationic Dye I)$^\oplus$ X$^\ominus$

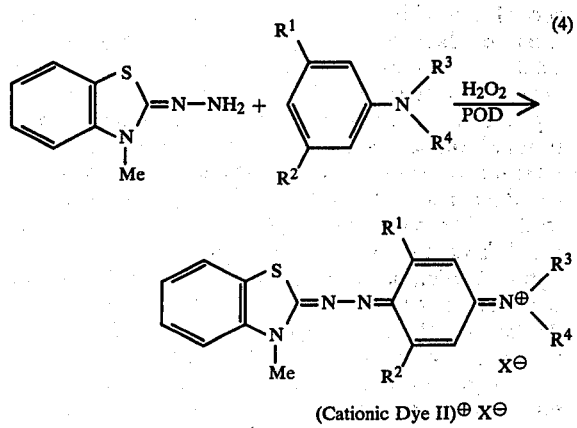

(4)

(Cationic Dye II)$^\oplus$ X$^\ominus$

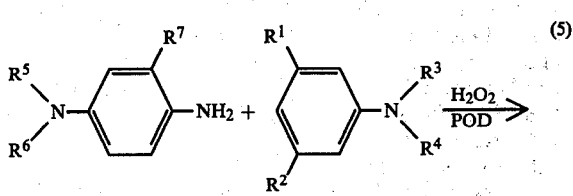

(5)

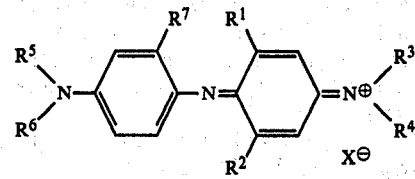

(Cationic Dye III)$^\oplus$ X$^\ominus$

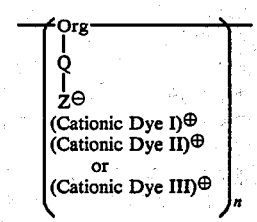

(6)

In formulae (3) to (6), $R^1$ to $R^7$ have the same meanings as in formula (1) or (2) and $X^\ominus$ represents an anion.

In formula (5), $Z^\ominus$ represents an atomic group containing a —COO$^\ominus$ or —SO$_3{}^\ominus$ or PO$_3{}^{2\ominus}$ group or an anionic polymer as earlier exemplified, $A^+$ represents a cation and n represents a positive integer.

The quantitative analysis film in accordance with the present invention comprises at least one reagent layer containing the color indicator for detecting hydrogen peroxide and the anionic polymer or comprises at least one color forming reaction layer containing the color indicator for detecting hydrogen peroxide and at least one dye-fixing layer containing the anionic polymer; the layer construction thereof can take various structures depending upon the purpose of use and the accuracy required for quantitative analysis.

Hereafter, the present invention will be described with reference to the drawings showing embodiments of the present invention.

FIG. 1 is a quantitative analysis film comprising reagent-impregnated support 23 obtained by impregnating a self-supporting porous support with a reagent composition containing the color indicator for detecting hydrogen peroxide and the anionic polymer on the surface thereof and in the interior thereof.

As self-supporting porous supports, known film-like or sheet-like supports such as a filter paper, conventional paper, non-woven cloth, membrane filter, a porous plastic film, etc., can be employed. In the case that the quantitative analysis film is to be installed in a slide frame as disclosed in Japanese Patent Application (OPI) Nos. 156079/79 and 160296/79, Japanese Utility Model Application No. 41787/80, Japanese Patent Application No. 138100/80, etc., flexible materials such as fabrics can also be employed in addition to the materials described above as the porous support. Such a quantitative analysis film can be employed by adhering it onto a film-like or sheet-like support using a hot melt adhesive or an adhesive tape and the layer structure in this case is similar to that of a quantitative analysis film shown in FIG. 2, which will subsequently be described.

Figure 2:
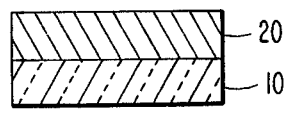

FIG. 2 shows a quantitative analysis film having such a structure that reagent layer 20 containing the color indicator for detecting hydrogen peroxide and the anionic polymer is provided on film-like or sheet-like support 10. The support 10 can be either transparent or opaque.

Figure 3:
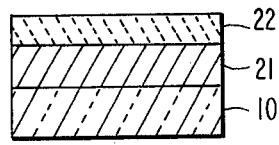

FIG. 3 shows a quantitative analysis film having such a structure that dye-fixing layer 21 containing the anionic polymer and color-forming reaction layer 22 containing the color indicator for detecting hydrogen peroxide are provided, in this sequence, on a film-like or sheet-like support. The support can be either transparent or opaque but it is preferably a transparent support.

In quantitative analysis films as shown in FIG. 4 through FIG. 8, a reagent layer, a color-forming reaction layer or a dye-fixing layer is provided between a support and a porous layer and the porous layer is brought into fluid contact (this definition is disclosed in Japanese Patent Application (OPI) No. 40191/76, ESP Application No. 0013156, etc., described above i.e., a mode of contact having the ability of a fluid, whether liquid of gaseous, to pass between layers) with the reagent layer, the color-forming layer or the dye-fixing layer; preferably, the analysis film has such a structure that these layers are adhered in a unitary or integral form.

The porous layer is employed as a porous spreading layer or a definite area-porous layer which have the function that when a sample liquid is spotted thereon the sample liquid is supplied onto a layer therebeneath and preferably has the function of rendering the quantity of the liquid sample per unit area approximately constant (in the case of the porous spreading layer), or which has the function of spreading into the same area of its shape to thereby render the quantity of the liquid sample per unit area approximately constant (in the case of the definite area-porous layer), in both cases the liquid sample being supplied to a layer therebeneath. In more detail, the latter porous layer has a definite area so that an amount of a liquid sample held in the porous layer is determined by the definite area and the thus determined amount of the liquid sample is transferred to a layer therebeneath (ordinarily a reagent layer) in the same amount and area as in the porous layer, since a possible expansion of the porous layer due to holding the liquid sample is negligible in the width direction when compared to the thickness direction.

It is sufficient that the porous layer has voids to provide transport of the liquid sample but in general, it is preferred that a void volume of the porous layer be in a range of from about 30 to about 85%. Void volume can be calculated by the technique described in Chalkley, *Journal of the National Cancer Institute*, vol. 4, page 47 (1943) and by direct weighing and determining the ratio of actual weight of the structure to the weight of solid material equal in volume to that of the structure.

Figure 4:
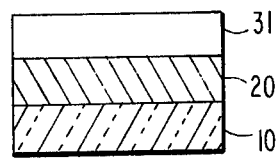

FIG. 4 shows a quantitative analysis film having a structure comprising film-like or sheet-like support 10 having provided thereon reagent layer 20 containing the color indicator for detecting hydrogen peroxide and the anionic polymer and porous spreading layer 31, in this sequence.

Figure 5:
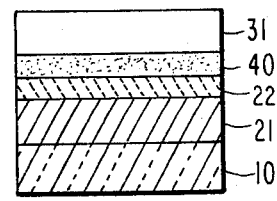

FIG. 5 shows a quantitative analysis film comprising film-like or sheet-like support 10 having provided thereon dye-fixing layer 21 containing the anionic polymer, color-forming reaction layer 22 containing the color indicator for detecting hydrogen peroxide, light-reflecting layer 40 and porous spreading layer 31, in this sequence.

As the porous spreading layer of the quantitative analysis film shown in FIG. 4 or FIG. 5, a porous layer having dispersed therein finely divided porous powders such as blush polymer (generally called, membrane filters) as desclosed in Japanese Patent Application (OPI) No. 53888/74 (corresponding to U.S. Pat. No. 3,992,158), diatomaceous earth, microcrystalline materials (e.g., microcrystalline cellulose (Avicel, tradename of FMC Corporation)) in a binder polymer, porous aggregates formed by allowing fine spherical beads of glass or polymers to adhere to one another in pointtopoint contact; a non-fibrous isotropic porous layer such as an aggregated three-dimensional lattice particle structure formed by allowing fine spherical beads of water-nonswellable organic polymers to adhere to one another using a water-insoluble adhesive in point-to-point contact, etc., as disclosed in Japanese Patent Application (OPI) No. 90589/80 (corresponding to U.S. Pat. No. 4,258,001); a fibrous anisotropic layer comprising fabrics rendered hydrophilic as disclosed in Japanese Patent Application (OPI) No. 164356/80 (corresponding to U.S. Pat. No. 4,292,272), fabrics which are rendered physically hydrophilic (e.g., by a glow discharge, a plasma treatment, corona discharge, ultraviolet irradiation, a flame treatment etc.) as disclosed in Japanese Patent Application (OPI) No. 140532/80, filter paper, etc.; can be employed.

The method for providing a non-fibrous isotropic porous layer onto reagent layer 20 or light-reflecting layer 40 as a porous spreading layer can be in accordance with the techniques disclosed in Japanese Patent Application (OPI) Nos. 53888/74 (corresponding to U.S. Pat. No. 3,992,158), 90589/80 (corresponding to U.S. Pat. No. 4,258,001), etc., described above on a method for providing the fibrous anisotropic porous spreading layer onto reagent layer 20 or light-reflecting layer 40 as a porous spreading layer can be in accordance with the techniques disclosed in Japanese Patent Application (OPI) No. 164356/80 and Japanese Patent Application No. 140532/80 described above.

The definite area-porous layer can be provided using materials (e.g., fabrics, paper, membrane filters) and in accordance with the method disclosed for the porous layer in Japanese Utility Model Application No. 120299/80. As materials for the definite area-porous layer, the same materials as used for the porous spreading layer can be employed and, in addition thereto, any material can be employed so long as the interior of the material is porous and can retain a liquid such as water and the pores thereof penetrate from one major surface to the other major surface. The method for providing the definite area-porous layer onto a reagent layer, a light-reflecting layer, or the like can be in accordance with the method disclosed in Japanese Utility Model Application No. 120299/80 or the method for providing the porous spreading layer described above.

As light-reflecting layer 40 (thickness 2-15 mu), a layer having dispersed one or more white pigments such as finely divided titanium dioxide powder, finely divided barium sulfate powder or the like in a hydrophilic binder polymer as disclosed in Japanese Patent Application (OPI) Nos. 53888/74 (corresponding to U.S. Pat. No. 3,992,158), 40191/76 (corresponding to U.S. Pat. No. 4,042,335), 164356/80 (corresponding to U.S. Pat. No. 4,292,272), etc., a blush polymer layer (membrane filter) having dispersed therein one or more white pigments such as finely divided titanium dioxide powder, finely divided barium sulfate powder or the like as disclosed in Japanese Patent Application (OPI) No. 53888/74 (corresponding to U.S. Pat. No. 3,992,158), etc., a blush polymer layer as disclosed in Japanese Patent Application (OPI) No. 53888/74 (corresponding to U.S. Pat. No. 3,992,158) etc., a water-permeable layer comprising a porous metal layer as disclosed in Japanese Patent Application (OPI) No. 26428/80, a water-permeable layer containing one or more metal powders as disclosed in Japanese Patent Application (OPI) No. 26429/80, etc. can be employed; techniques for providing these layers can be in accordance with the methods as disclosed in the specifications described above.

Figure 6:
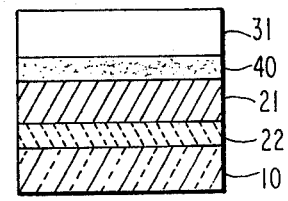

FIG. 6 shows a quantitative analysis film having a structure comprising support 10 having provided thereon, in sequence, color-forming reaction layer 22 containing the color indicator for detecting hydrogen peroxide, dye-fixing layer 21 containing the anionic polymer, light-reflecting layer 40 and porous spreading layer 31 and has a structure such that the positional relationship of the color-forming reaction layer to the dye-fixing layer is reversed in the quantitative analysis film shown in FIG. 5. The positional relationship of the color-forming reaction layer to the dye-fixing layer can be freely chosen except that cationic compound that absorbs light at the wavelength region (generally about 400 to about 700 nm) at which the cationic dye formed by the color indicator for detecting hydrogen peroxide absorbs should not be used as such interferes with colorimetric analysis. Accordingly, this positional relationship is effective in the case where it is desired to provide the color-forming reaction layer as a lower layer so that it will not contact the air, e.g, where a component in the color indicator for detecting hydrogen peroxide might be oxidized by air, etc.

Figure 7:
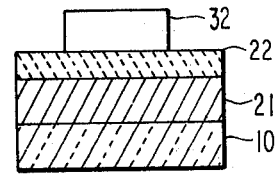

FIG. 7 indicates a quantitative analysis film having a structure comprising support 10 having provided thereon, in sequence, dye-fixing layer 21 containing the anionic polymer, color-forming reaction layer 22 containing the color indicator for detecting hydrogen peroxide and further thereon a porous layer which is porous and has a definite area which is determined so that a liquid sample can be supplied thereto in an amount greater than that of water which can be held in the porous layer and transferred into color forming reaction layer 22 in the thus determined amount of the liquid sample with the same width as that of layer 32, i.e., definite area-porous layer 32 in close contact. A quantitative analysis film having a definite area-porous layer is suited for analysis of the hydrogen peroxide content in an aqueous liquid sample particularly containing a small quantity of hydrogen peroxide contained. A light-reflecting layer can be provided between a color-forming reaction layer and a definite area-porous layer. Further, the location of a colorforming reaction layer and a dye-fixing layer can also be reversed (as in the case of the quantitative analysis film as shown in FIG. 6).

Figure 8:
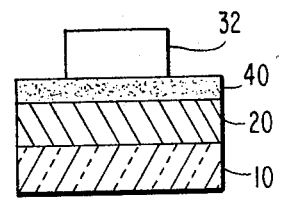

FIG. 8 indicates a quantitative analysis film having a structure comprising support 10 having provided thereon, in sequence, reagent layer 20 containing the color indicator for detecting hydrogen peroxide and the anionic polymer, light-reflecting layer 40 and definite area-porous layer 32. In FIG. 7 and FIG. 8, the definite area-porous layer is illustrated to have a size smaller than those of the other layers; however, it is sufficient if the definite area-porous layer is designed to have a shape and size of not greater than those of the color-forming reaction layer or the reagent layer and accordingly, the definite area-porous layer may have the same shape and size as the color-forming reaction layer or the reagent layer, as shown in FIG. 8.

As supports for the quantitative analysis films as shown in FIGS. 3 through 8, films or sheets of a variety of polymers such as polyethylene terephthalate, cellulose esters (cellulose diacetate, cellulose triacetate, cellulose acetate propionate, etc.), polycarbonates (polycarbonate of bisphenol A, etc.), polymethyl methacrylate, polystyrene, etc., having a thickness of about 25 $\mu m$ to about 0.3 mm, preferably about 50 $\mu m$ to about 0.2 mm, can be employed.

Supports which are colorless transparent or transparent to light having wavelengths which the cationic dye formed from the color indicator for detecting hydrogen peroxide absorbs can be employed. In addition, supports which are rendered light-blocking by incorporating pigments therein (e.g., finely divided titanium oxide powder, finely divided barium sulfate powder, finely divided zinc oxide powder, carbon black), etc., can also be employed. In the case that light-blocking supports are employed, colorimetric measurement can be performed after stripping off and removing the support upon colorimetric measurement by measuring reflection light from the side free of the support. The use of a light-blocking support is advantageous in the case where reagent components liable to be photodecomposed are incorporated into a reagent layer, a color-forming reaction layer or a dye-fixing layer.

The reagent layer, the color-forming reaction layer or the dye-fixing layer of the quantitative analysis film in accordance with the present invention can contain an analyte component which differs from hydrogen peroxide (hereafter referred to as an "analyte precursor component") and a reagent composition system capable of forming hydrogen peroxide through chemical reaction (hereafter referred to as "reagent system for forming hydrogen peroxide"). Alternatively, a reagent layer containing the reagent system for forming hydrogen peroxide (hereafter referred to as an "hydrogen peroxide-forming reagent layer") can also be provided separately from the reagent layer, the color-forming reaction layer or the dye-fixing layer. The hydrogen peroxide-forming reagent layer can be any reagent composition system in which hydrogen peroxide is produced from the analyte precursor component through chemical reaction in one step or a reagent composition system in which hydrogen peroxide is produced from the analyte precursor component through chemical reactions comprising continuous enzyme reactions (e.g., cholesterol ester $\xrightarrow{\text{cholesterol esterase}}$ cholesterol $\xrightarrow{\text{cholesterol oxidase}} H_2O_2$)

in a plurality of steps. Depending upon the hydrogen peroxide-forming reagent system, the reagent system for forming hydrogen peroxide can be incorporated into the reagent layer, the color-forming reaction layer or the dye-fixing layer, or a single layer or a pluraling of layers different from the aforesaid layer can be provided as the hydrogen peroxide-forming reagent layer. Such is well known to one skilled in the art.

Examples of analyte precursor components and reagent systems for forming hydrogen peroxide include a system comprising cholesterol esters and cholesterol (as analyte precursors; hereafter the same)—cholesterol esterase and cholesterol oxidase (as the reagent system for forming hydrogen peroxide; hereafter the same) as disclosed in Japanese Patent Application (OPI) Nos. 137192/75 (corresponding to U.S. Pat. No. 3,983,005), 131588/75 (corresponding to U.S. Pat. No. 3,869,349), 124499/80 (corresponding to U.S. Pat. No. 4,269,938), etc.; a system comprising glucose-glucose oxidase as disclosed in Japanese Patent Application (OPI) Nos. 53888/74 (corresponding to U.S. Pat. No. 3,992,158), 40191/76 (corresponding to U.S. Pat. No. 4,042,335), 124499/80 (corresponding to U.S. Pat. No. 4,269,938), 164356/80, etc.; a system comprising triglycerides-glycerine, lipase, glycerine kinase, α-glycerophosphate oxidase, etc. as disclosed in Japanese Patent Application (OPI) Nos. 24892/78 (corresponding to U.S. Pat. No. 4,241,178), 24893/78, 26382/78 (corresponding to U.S. Pat. No. 4,179,334), etc.; a system comprising lactic acid salts and lactic acid-lactate dihydrogenase and lactate oxidase as disclosed in Japanese Patent Application (OPI) Nos. 105292/78, 73096/79 (corresponding to U.S. Pat. No. 4,184,923), etc.; a system comprising urikase and a hydrogen peroxide-forming reagent capable of reacting with or containing any one of the foregoing substances as disclosed in U.S. Pat. No. 4,062,731, Japanese Patent Application (OPI) Nos. 50393/79 (corresponding to U.S. Pat. No. 4,283,491), 124499/80 (corresponding to U.S. Pat. No. 4,269,938), etc. Needless to say, the analyte precursor components and the hydrogen peroxide-forming reagent systems are not limited to those as described above and other hydrogen peroxide-forming reagent systems for analyte precursor components can also be employed.

In the case that the quantitative analysis film of the present invention—including the embodiments shown in FIGS. 2 through 8—takes a multi-layered composite structure, methods as disclosed in Japanese Patent Application (OPI) Nos. 53888/74 (corresponding to U.S. Pat. No. 3,992,158), 40191/76 (corresponding to U.S. Pat. No. 4,042,335), 90859/80 (corresponding to U.S. Pat. No. 4,258,001) and 164356/80, Japanese Patent Application No. 140532/80, Japanese Patent Application (OPI) Nos. 26428/80 and 26429/80, Japanese Utility Model Application No. 120299/80, etc., described above can ve used to form the same; alternatively, the quantitative analysis film can be prepared using known various coating techniques established as methods for preparing conventional color photographic light sensitive materials, instant black-and-white or color photographic light sensitive materials as they are or by slightly modifying the same.

A method for quantitatively assaying hydrogen peroxide using the quantitative analysis film of the present invention will be explained below. Procedures for quantitative analysis using the quantitative analysis film of the present invention include dropping a liquid sample to be tested onto the quantitative analysis film, measurement of the optical density of a color formed on the dye-fixing layer and incubation after spotting depending upon necessity. Dropping and incubation of a liquid sample to be tested can be performed under conventional conditions (generally at temperatures of from about 15° to about 40° C. for 2 to 20 mins. using equipments for dropping a sample liquid and measurement devices in accordance with the method disclosed in the aforesaid patent specifications or Japanese Patent Application (OPI) Nos. 81292/78 (corresponding to U.S. Pat. No. 4,224,032), 76044/78 (corresponding to U.S. Pat. No. 4,119,381) and 76095/78 (corresponding to U.S. Pat. No. 4,152,390), Japanese Patent Application No. 154313/79, Japanese Utility Model Application Nos. 45527/80 and 103204/80, etc. In the case the quantitative analysis films have structures as shown in FIGS. 4 to 8, quantitative analysis can be performed with extremely high accuracy by dropping a trace amount of a sample liquid within the range of from 5 μl to 50 μl. On the other hand, in the case that the quantitative analysis films as shown in FIGS. 1 through 3 are employed, quantitative analysis can be performed by immersing the quantitative analysis films in a sample liquid to be tested, remaining them, if necessary, incubating the same and then subjecting to colorimetric measurement. In this case, analysis can be performed using devices for colorimetric measurement as disclosed in Japanese Patent Application (OPI) Nos. 82685/76 and 144293/76, Japanese Utility Model Application (OPI) No. 134381/77, etc.

Having thus generally described the invention, the following Examples are given to further illustrate the same.

EXAMPLE 1

| Composition of Coating Solution for Reagent Layer: | |
|---|---|
| N—(2-Cyanoethyl)-N—(2-hydroxyethyl)-m-toluidine | 7 mg. |

HO—CH$_2$CH$_2$\\N/CH$_2$CH$_2$—CN (attached to benzene ring with CH$_3$)

| | |
|---|---|
| Dimedone | 2 mg. |
| 4-Aminoantipyrine | 8 mg. |
| Phosphate buffer (pH 7.0), 0.2M | 500 μl. |
| Potassium polystyrene4-sulfonate | 10 mg. |
| Gelatin | 500 mg. |
| POD (peroxidase) | 300 Units |
| 1 wt % Aqueous solution of Bis (vinylsulfonyl-methyl)ether | 500 mg. |
| Surfactant 10 G | 5 mg. |

(50 wt % aqueous solution containing as a main ingredient:

n-C$_9$H$_{19}$—⟨benzene⟩—O$+$CH$_2$CHCH$_2$O$)_{10}$H)
                                       |
                                      OH The coating solution described above was coated onto a colorless transparent polyethylene terephthalate (PET) film (thickness, 180 μm) for photographic film in a layer thickness of 20 μm after drying.

| Composition of Coating Solution of Titanium Dioxide Layer (Light-Reflecting layer) | |
|---|---|
| Finely divided TiO$_2$ powder | 19.5 g. |
| Gelatin | 6.8 g. |
| Dioctyl sodium sulfosuccinate | 1.0 g. |
| Water | 87 g. |

Then, a titanium dioxide layer was coated as an adhesive layer in contact with the reagent layer in a layer thickness of 7 μm after drying.

Lastly, the adhesive layer was wet with water and a smooth filter paper having a thickness of 200 μm for chromatographic use was put thereon followed by pressing the same to insure adhesion.

Whereby, a multi-layered quantitative analysis film for detecting hydrogen peroxide was prepared.

This film was cut into units of 0.5 cm² in area and 20 μl samples of an aqueous solution of hydrogen peroxide having various concentrations prepared according to a standard method were dropped onto the uppermost filter paper of various units. The optial density of color formed after 5 mins. at 37° C. was measured as reflection optical density through the support.

| Concentration of Hydrogen Peroxide in Aqueous Solution of Hydrogen Peroxide (mol/l) | Reflection Optical Density (value obtained by measurement through a green filter) |
|---|---|
| 0 | 0.166 |
| $10^{-4}$ | 0.358 |
| $5 \times 10^{-4}$ | 1.034 |
| $10^{-3}$ | 1.723 |

COMPARISON EXAMPLE 1

For purpose of comparison, a multilayer quantitative analysis film was prepared in a manner similar to Example 1 except that polystyrene-4-potassium sulfonate was omitted from the coating solution for the reagent layer of Example 1; the units were otherwise identical to those of Example 1, whereafter analysis, etc., similar to Example 1 was performed.

| Concentration of Hydrogen Peroxide in Aqueous Solution of Hydrogen Peroxide (mol/l) | Reflection Optical Density (value obtained by measurement through a green filter) |
|---|---|
| 0 | 0.168 |
| $10^{-4}$ | 0.205 |
| $5 \times 10^{-4}$ | 0.413 |
| $10^{-3}$ | 0.712 |

EXAMPLE 2

A multi-layered quantitative analysis film was prepared in a manner similar to Example 1 except for using as the N,N-disubstituted anilines:

N—Ethyl-N—2-hydroxyethyl-m-toluidine (1)

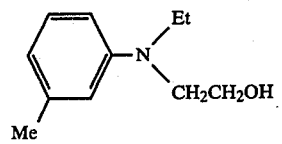

N,N—Bis(2-hydroxyethyl)-m-toluidine (2)

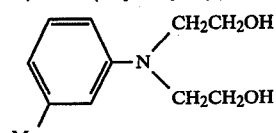

N,N—Bis(2-hydroxypropyl)-m-toluidine (3)

-continued

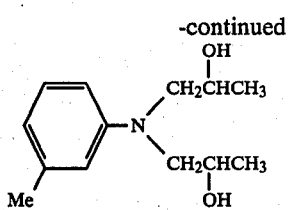

2-(N—Ethylanilino)ethanol (4)

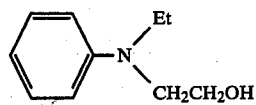

N,N—Dimethyl-m-toluidine (5)

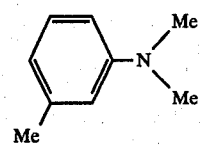

N,N—Dimethyl-m-anisidine (6)

Onto the analysis film, 20 μl. of an aqueous solution of hydrogen peroxide having a concentration of $5 \times 10^{-4}$ mol/l was dropped and the system was incubated at 37° C. for 5 mins. to form a color. Optical densities of the formed color were as follows:

| N,N—Disubstituted Aniline | Reflected Optical Density (value measured through a green filter) |
|---|---|
| (1) | 1.205 |
| (2) | 1.103 |
| (3) | 0.744 |
| (4) | 0.812 |
| (5) | 0.581 |
| (6) | 0.637 |

EXAMPLE 3

A quantitative analysis film was prepared in a manner to Example 1 except that N,N-diethyl-p-phenylenediamine was employed as a hydrogen donor and N,N-bis(2-hydroxyethyl)-m-toluidine was employed as an N,N-disubstituted aniline. Onto the filter paper of the analysis film, 20 μl of an aqueous solution of hydrogen peroxide having a concentration of $5 \times 10^{-4}$ mol/l and incubated at 37° C. for 5 mins. to form a color. The density of the formed color was measured through the PET film. The optical density was 0.75 with near infrared light having wavelength of 740 nm.

EXAMPLE 4

Quantitative analysis films A, B, C and D

Solutions of indicators for detecting hydrogen peroxide having composition as shown below were coated onto a colorless transparent PET film for photographic use having a thickness of 180 μm, respectively, in a thickness of 20 μm after drying, and then dried to provide reagent layers.

TABLE 1

| Component | Quantitative Analysis Film | | | |
|---|---|---|---|---|
| | A | B | C | D |
| Gelatin (g) | 5 | 5 | 5 | 5 |
| N,N—Bis(2-hydroxyethyl)-m-toluidine (mg) | 120 | 120 | 120 | 120 |
| 4-Aminoantipyrine (mg) | 120 | 120 | 120 | 120 |
| 0.2 M Phosphate Buffer (pH 7.2) (ml) | 10 | 10 | 10 | 10 |
| POD (U) | 1500 | 1500 | 1500 | 1500 |
| Bis(Vinylsufonylmethyl) ether,1 wt % aq. solution (ml) | 10 | 10 | 10 | 10 |
| Surfactant 10 G (earlier defined) (mg) | 300 | 300 | 300 | 300 |
| Water (ml) | 30 | 30 | 30 | 30 |
| Polystyrene-p-potassium sulfonate (mg) | — | 100 | 250 | 500 |

A light-reflecting layer having a dry thickness of 7 μm was then provided on the respective reagent layers as per Example 1. Lastly, a circular piece of filter paper having a thickness of 400 μm and an area on the side in contact with the light-reflecting layer (bottom area) of 50 mm² was placed on the light-reflecting layer (as a fixed area-porous layer) to complete quantitative analysis films A, B, C and D.

Qauntitative analysis film E

A solution for a dye-fixing layer having the following composition was coated onto a colorless transparent PET film having a thickness of 180 μm for photographic use in a dry thickness of 5 μm followed by drying to thereby provide the dye-fixing layer.

| Composition of solution for dye-fixing layer: | |
|---|---|
| Potassium polystyrene-p-sulfonate | 5 g. |
| Gelatin | 5 g. |
| Surfactant 10 G | 1 g. |
| Water | 100 ml. |

Then, a solution of an indicator for detecting hydrogen peroxide having the same composition as used for quantitative film A was coated on the dye-fixing layer in a dry thickness of 20 μm and dried to provide a color-forming reaction layer. Thereafter, a light-reflecting layer (thickness, 7 μm) and a piece of filter paper (thickness, 400 μm; bottom area, 50 mm²) as per film A were placed on the color-forming reaction layer as per film A to complete quantitative analysis film E.

Quantitative analysis film F

A solution of the indicator for detecting hydrogen peroxide having the same composition as was used for quantitative analysis film A was coated on a colorless transparent PET film for photographic use having a thickness of 180 μm in a dry thickness of 20 μm and dried to form a color-forming reaction layer. Then, a solution for the dye-fixing layer having the same composition as was used for quantitative analysis film E was coated on the color-forming reaction layer in a dry thickness of 5 μm and dried to provide a dyefixing layer. Thereafter, a light-reflecting layer (thickness, 7 μm) and a piece of filter paper (thickness, 400 μm; bottom area, 50 mm²) as per film A were placed on the dye-fixing layer in a manner similar to film A to complete quantitative analysis film F.

Colorimetric Measurement

On each piece of the filter paper of the six quantitative analysis films obtained as described above, 20 μl each of an aqueous solution of hydrogen peroxide having a hydrogen peroxide concentration of $1\times10^{-3}$M was dropped and attached thereto. After dropping, reflection optical densities were measured for all of the quantitative analysis films, when incubated at 37° C. for 6 mins., at a wavelength of 600 nm through the PET film. Measurement values were as follows:

| | Concentration of Hydrogen Peroxide | |
|---|---|---|
| | $1\times10^{-3}$ M | $5\times10^{-3}$ M |
| Quantitative Analysis | | |
| Film A (comparison) | 0.46 | 0.59 |
| Film B (invention) | 0.82 | 1.09 |
| Film C (invention) | 1.06 | 1.40 |
| Film D (invention) | 1.26 | 1.67 |
| Film E (invention) | 1.35 | 1.95 |
| Film F (invention) | 1.41 | 2.10 |

From the measurement results, the following is made clear.

The reflection optical density value of the reagent layer was small with quantitative analysis film A (Comparison Example) which comprised no layer containing the anionic polymer because the dye formed diffused into the light-reflecting layer and into the filter paper.

In quantitative analysis films B, C and D (present invention) comprising the reagent layer containing the anionic polymer, the reflection optical density values increased as the content of the anionic polymer increased since the dye formed was bound and fixed to the anionic polymer in the reagent layer and the amount of the dye diffused into the light-reflecting layer and the filter paper piece was reduced.

Further, in quantitative analysis films E and F (present invention) in which the dye-fixing layer containing the anionic polymer was provided in contact with the color-forming reaction layer free of the anionic polymer, the dye formed in the color-forming reaction layer was bound and fixed to the anionic polymer contained in the dye-fixing layer in contact therewith, and the dye diffused into the light-reflecting layer and the filter paper piece was markedly reduced so that the optical density values of the dye-fixing layer increased. The dye-fixing layer could effectively fix the formed dye both on the side remote from the sample liquid (quantitative analysis film E) and on the side near the same (quantitative analysis film F), with respect to the color-forming reaction layer.

While the invention has been described in detail and with reference to specific embodiments thereof, it will be apparent to one skilled in the art that various changes and modifications can be made therein without departing from the spirit and scope thereof.

What is claimed is:

1. A quantitative analysis film comprising a reagent layer containing a N,N-disubstituted aniline cationic dye-forming color indicator composition for detecting hydrogen peroxide comprising components capable of forming said colored cationic dye by chemical interaction in the presence of hydrogen peroxide, and an anionic polymer capable of reacting with the formed cationic dye to fix the formed dye.

2. The quantitative analysis film as claimed in claim 1, wherein said cationic dye has the following formula (CD):

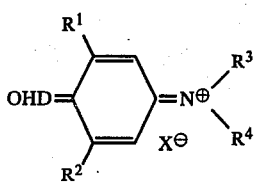 (CD)

wherein $R^1$ and $R^2$ each represents a hydrogen atom, an alkyl group or an alkoxy group and $R^1$ and $R^2$ may be the same or different from each other; $R^3$ and $R^4$ represent an alkyl group, an alkoxyalkyl group, a hydroxyalkyl group, an aminoalkyl group, a cyanoalkyl group, a halogenoalkyl group or an acylaminoalkyl group and $R^3$ and $R^4$ may be the same or different from each other, wherein OHD is an oxidized hydrogen donor moiety.

3. The quantitative analysis film as claimed in claim 1, wherein said anionic polymer has the following formula (AP):

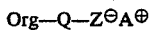 (AP)

wherein Org represents an organic group which constitutes a portion of the anionic polymer backbone, Q represents a chemical bond(s) or a chemical group linking $Z^\ominus$ to Org, $Z^\ominus$ represents a carboxylate group, ($-COO^\ominus$), a sulfonate group ($-SO_3^\ominus$) or a phosphonate group ($-PO_3^{2\ominus}$) and $A^\oplus$ is a counter cation.

4. The quantitative analysis film as claimed in claim 1 wherein said components capable of forming said cationic dye are non-ionic.

5. The quantitative analysis film as claimed in claim 1 wherein said reagent layer comprises a color-forming reaction layer containing said color indicator composition and a dye-fixing layer comprising said anionic polymer.

6. The quantitative analysis film as claimed in claim 1 wherein said reagent layer is a single layer.

7. The quantitative analysis film as claimed in claim 1, 5, or 6 wherein said reagent layer is provided between a support and a porous layer and said porous layer and said reagent layer are adhered to one another as an integral composite in fluid contact with each other.

8. The quantitative analysis film as claimed in claim 1, wherein said color indicator composition is a color indicator composition comprising, as main ingredients, a substance having a peroxidase activity, a hydrogen donor and said N,N-disubstituted aniline.

9. The quantitative analysis film as claimed in claim 8 wherein said hydrogen donor is a compound selected from the group consisting of a compound represented by formula (2), a 4-substituted antipyrine, a 2-hydrazonobenzothiazoline and a p-halogenophenol:

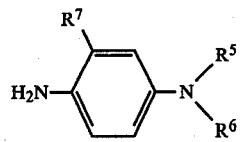 (2)

wherein $R^5$ and $R^6$ each represents an alkyl group, an alkoxyalkyl group, a hydroxyalkyl group, a cyanoalkyl group, a halogenoalkyl group or an acylaminoalkyl group and $R^5$ and $R^6$ may be the same or different; and $R^7$ represents a hydrogen atom, an alkyl group, an alkoxy group or a halogen atom.

10. The quantitative analysis film as claimed in claim 9 wherein said hydrogen donor is 4-aminoantipyrine.

11. The quantitative analysis film as claimed in claim 8 wherein said anionic polymer is a polymer containing a carboxylate group, a sulfonate group or a phosphonate group.

12. The quantitative analysis film as claimed in claim 8 or 11 wherein said N,N-disubstituted aniline is a compound represented by formula (1):

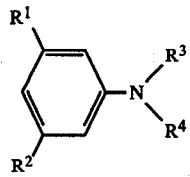 (1)

wherein $R^1$ and $R^2$ each represents a hydrogen atom, an alkyl group or an alkoxy group and $R^1$ and $R^2$ may be the same or different; $R^3$ and $R^4$ each represents an alkyl group, an alkoxyalkyl group, a hydroxyalkyl group, an aminoalkyl group, a cyanoalkyl group, a halogenoalkyl group or an acylaminoalkyl group and $R^3$ and $R^4$ may be the same or different.

13. A method for quantitatively assaying hydrogen peroxide of a precursor capable of forming hydrogen peroxide contained in a test sample colorimetrically which comprises bringing said test sample into contact with a N,N-disubstituted aniline cationic dye-forming color indicator for detecting hydrogen peroxide comprising components capable of forming said colored cationic dye by chemical mutual action in the presence of hydrogen peroxide and then binding the cationic dye formed to an anionic polymer to fix the formed cationic dye.

14. The method for quantitatively assaying colorimetrically as claimed in claim 13 wherein said anionic polymer is present with said color indicator composition for detecting hydrogen peroxide prior to formation of the cationic dye.

15. The method for quantitatively assaying colorimetrically as claimed in claim 13 wherein said anionic polymer is brought into contact with and bound to said cationic dye after the cationic dye is formed.

16. The method for quantitatively assaying colorimetrically as claimed in claim 13, wherein said cationic dye has the following formula (CD):

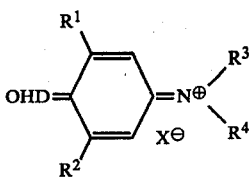 (CD)

wherein $R^1$ and $R^2$ each represents a hydrogen atom, an alkyl group or an alkoxy group and $R^1$ and $R^2$ may be the same or different from each other; $R^3$ and $R^4$ represent an alkyl group, an alkoxyalkyl group, a hydroxyalkyl group, an aminoalkyl group, a cyanoalkyl group, a halogenoalkyl group or an acylaminoalkyl group and $R^3$ and $R^4$ may be the same or different from each other, wherein OHD is an oxidized hydrogen donor moiety.

17. The method for quantitatively assaying colorimetrically as claimed in claim 13, wherein said anionic polymer has the following formula (AP):

$$\text{Org}-\text{Q}-\text{Z}^{\ominus}\text{A}^{\oplus} \qquad \text{(AP)}$$

wherein Org represents an organic group which constitutes a portion of the anionic polymer backbone, Q represents a chemical bond(s) or a chemical group linking $Z^{\ominus}$ to Org, $Z^-$ represents a carboxylate group, ($-COO^{\ominus}$), a sulfonate group ($-SO_3^{\ominus}$) or a phosphonate group ($-PO_3^{2\ominus}$) and $A^{\oplus}$ is a counter cation.

18. The method for quantitatively assaying colorimetrically as claimed in claim 13 wherein said components capable of forming said cationic dye are non-ionic.

* * * * *